United States Patent
Markosyan

(10) Patent No.: US 11,533,939 B2
(45) Date of Patent: *Dec. 27, 2022

(54) **FOOD INGREDIENTS FROM *STEVIA REBAUDIANA***

(71) Applicant: PureCircle Sdn Bhd, Negeri Sembilan (MY)

(72) Inventor: Avetik Markosyan, Kuala Lumpur (MY)

(73) Assignee: PURECIRCLE SDN BHD, Negeri Sembilan (MY)

( * ) Notice: Subject to any disclaimer, the term of this patent is extended or adjusted under 35 U.S.C. 154(b) by 720 days.

This patent is subject to a terminal disclaimer.

(21) Appl. No.: 16/449,467

(22) Filed: Jun. 24, 2019

(65) Prior Publication Data

US 2019/0357577 A1   Nov. 28, 2019

Related U.S. Application Data

(62) Division of application No. 13/943,776, filed on Jul. 16, 2013, now Pat. No. 10,368,570, which is a division of application No. 13/530,113, filed on Jun. 22, 2012, now Pat. No. 8,530,527.

(60) Provisional application No. 61/500,598, filed on Jun. 23, 2011.

(51) Int. Cl.

| A23L 33/125 | (2016.01) |
| A23L 5/00 | (2016.01) |
| A23L 29/00 | (2016.01) |
| A23L 29/10 | (2016.01) |
| A23L 29/20 | (2016.01) |
| A23L 29/212 | (2016.01) |
| A23L 29/262 | (2016.01) |
| A23L 29/30 | (2016.01) |
| A23L 27/10 | (2016.01) |
| A23L 27/30 | (2016.01) |
| A23L 5/40 | (2016.01) |
| A23L 33/105 | (2016.01) |
| A23L 33/175 | (2016.01) |
| A23L 33/21 | (2016.01) |
| A23L 2/60 | (2006.01) |
| A61Q 19/00 | (2006.01) |
| C08B 15/02 | (2006.01) |
| A23L 27/29 | (2016.01) |
| A61K 8/9789 | (2017.01) |
| A61K 8/9794 | (2017.01) |
| A23L 7/00 | (2016.01) |

(52) U.S. Cl.
CPC .............. *A23L 33/125* (2016.08); *A23L 2/60* (2013.01); *A23L 5/00* (2016.08); *A23L 5/40* (2016.08); *A23L 27/10* (2016.08); *A23L 27/11* (2016.08); *A23L 27/29* (2016.08); *A23L 27/30* (2016.08); *A23L 27/32* (2016.08); *A23L 27/33* (2016.08); *A23L 27/35* (2016.08); *A23L 27/36* (2016.08); *A23L 27/37* (2016.08); *A23L 29/00* (2016.08); *A23L 29/10* (2016.08); *A23L 29/20* (2016.08); *A23L 29/212* (2016.08); *A23L 29/262* (2016.08); *A23L 29/30* (2016.08); *A23L 29/35* (2016.08); *A23L 29/37* (2016.08); *A23L 33/105* (2016.08); *A23L 33/175* (2016.08); *A23L 33/21* (2016.08); *A61K 8/9789* (2017.08); *A61K 8/9794* (2017.08); *A61Q 19/00* (2013.01); *C08B 15/02* (2013.01); *A23L 7/00* (2016.08); *A23V 2002/00* (2013.01); *A23V 2200/132* (2013.01); *A23V 2200/15* (2013.01); *A23V 2250/262* (2013.01)

(58) Field of Classification Search
None
See application file for complete search history.

(56) References Cited

U.S. PATENT DOCUMENTS

| 4,082,858 A | 4/1978 | Morita et al. |
| 4,361,697 A | 11/1982 | Dobberstein et al. |
| 4,892,938 A | 1/1990 | Giovanetto |
| 5,962,678 A | 10/1999 | Payzant et al. |
| 5,972,120 A | 10/1999 | Kutowy et al. |
| 7,838,044 B2 | 11/2010 | Abelyan et al. |
| 7,862,845 B2 | 1/2011 | Magomet et al. |
| 2007/0116828 A1 | 5/2007 | Prakash et al. |

OTHER PUBLICATIONS

Ohwoavworhua et al (Indian J Pharm Sci 72:295-301, 2010) (Year: 2010).*
GRAS Assessment of Rebaudioside A (Jan. 19, 2009) (Year: 2009).*
Oluwasina et al (BioResources 9:6166-6192, 2014) (Year: 2014).*
Altrista et al (J Young Pharm 10(Suppl S2):s79-s83, 2018) (Year: 2018).*
GRAS notification for Rebaudioside A, Jan. 19, 2009.
Stevia: The Journey from GRAS to Grocery (Webinar dated May 12, 2010).
PureVia website, http://www.purevia.com/nature/stevia.aspx accessed online Jan. 13, 2016.
Ash et al., Handbook of Fillers, Excipients and Diluents, 2nd Ed., 2007, p. 187.
Ohwoavworhua et al., Indian J. Pharm Sci 72:295-301, 2010.
Oluwasina et al., BioResources 9:6166-6192, 2014.
Altrista et al., J. Young Pharm 10 (Suppl S2) s79-s83, 2018.

* cited by examiner

*Primary Examiner* — Craig D Ricci
(74) *Attorney, Agent, or Firm* — Rachael Casey

(57) ABSTRACT

Various ingredients and compositions are prepared from *Stevia rebaudiana* Bertoni plant. The compositions can be used as bulking agents, and sweeteners in foods, beverages, cosmetics and pharmaceuticals.

13 Claims, No Drawings

FOOD INGREDIENTS FROM *STEVIA REBAUDIANA*

RELATED APPLICATION

This application is a divisional application of U.S. patent application Ser. No. 13/943,776 filed Jul. 16, 2013, which is a divisional application of U.S. patent application Ser. No. 13/530,113 filed Jun. 22, 2012 and granted as U.S. Pat. No. 8,530,527, which in turn claims the benefit under 35 U.S.C. 119(e) of U.S. provisional application no. 61/500,598 filed Jun. 23, 2011, which are herein incorporated by references.

FIELD OF THE INVENTION

The invention relates to a process for producing food ingredients from Stevia rebaudiana Bertoni plant and their use in various food products and beverages.

BACKGROUND OF THE INVENTION

Nowadays sugar alternatives are receiving increasing attention due to awareness of many diseases in conjunction with consumption of high-sugar foods and beverages. However many artificial sweeteners such as dulcin, sodium cyclamate and saccharin were banned or restricted in some countries due to concerns on their safety. Therefore non-caloric sweeteners of natural origin are becoming increasingly popular. The sweet herb *Stevia rebaudiana* Bertoni produces a number of diterpene glycosides which feature high intensity sweetness and sensory properties superior to that of many other high potency sweeteners.

The above-mentioned sweet glycosides have a common aglycon, steviol, and differ by the number and type of carbohydrate residues at the C13 and C19 positions. The leaves of Stevia are able to accumulate up to 10-20% (on dry weight basis) steviol glycosides. The major glycosides found in Stevia leaves are rebaudioside A (2-10%), stevioside (2-10%), and rebaudioside C (1-2%). Other glycosides such as rebaudioside B, D, E, and F, steviolbioside and rubusoside are found at much lower levels (approx. 0-0.2%).

Methods for the extraction and purification of sweet glycosides from the *Stevia rebaudiana* plant using water or organic solvents are described in, for example, U.S. Pat. Nos. 4,361,697; 4,082,858; 4,892,938; 5,972,120; 5,962,678; 7,838,044 and 7,862,845.

As it is well known the use of high intensity sweeteners in various applications requires various bulking agents to substitute the sugar which is removed from the formulation. The bulking agents used in those applications include both caloric and non-caloric materials. Non limiting examples of bulking agents include fructooligosaccharides, inulin, inulooligosaccharides, maltooligosaccharides, maltodextrins, cyclodextrins, corn syrup solids, erythritol and other sugar alcohols, glucose, maltose, lactose, tagatose, lactulose, palatinose, isomalt, modified starches etc.

Obviously more preferable are the bulking agents which provide zero calories, such as erythritol, isomalt, fructooloigosacharides, inulin etc.

On the other hand it has to be noted that steviol glycosides are compounds extracted from the plant and in process of their manufacture large amounts of "empty" biomass is created. Moreover, generally, the extraction process utilizes only the Stevia plant leaves. This additionally generates large amount of the stems which have limited use as well. The "empty" biomass is mainly discharged directly to environment. In some cases it is used for biogas production. It might be used as biofertilizer as well. The stems are generally used as fuel.

There is no reports to-date on processing the stevia biomass into any food ingredient. Nevertheless, if accomplished in large scale, this can provide significant economic, and environmental benefits as it can provide an opportunity for inclusion of whole stevia plant into food chain, creating practically wasteless stevia processing.

Within the description of this invention we will show that, stevia plant biomass may be used as a source for producing valuable food ingredient, which can be used in number of food and beverage applications.

SUMMARY OF THE INVENTION

The present invention is aimed to overcome the disadvantages of existing Stevia processing industrial schemes. The invention describes a process for producing a high value food ingredient from the *Stevia rebaudiana* Bertoni plant and use thereof in various food products and beverages as a carrier or bulking agent.

The invention, in part, pertains to a food ingredient comprising cellulose, or cellulose containing biomass derived from *Stevia rebaudiana* Bertoni plant.

In the invention, *Stevia rebaudiana* Bertoni plants, particularly the leaves and stems, were used as a starting material.

The starting material was subjected to size reduction, by means of rotary blade milling machine. The grinded biomass was subjected to alkaline pulping, followed by chlorine-free bleaching and acid hydrolysis and spray drying to produce a microcrystalline cellulose complying to specifications prepared at the 55th JECFA (2000) and published in FNP52 Add 8 (2000).

The obtained products are applicable to various foods and beverages as bulking agent, including tabletop sweeteners, soft drinks, ice cream, cookies, bread, fruit juices, milk products, baked goods and confectionary products.

Preferably the product of invention is used with other sweeteners, flavors and food ingredients.

Non-limiting examples of sweeteners include steviol glycosides, stevioside, rebaudioside A, rebaudioside B, rebaudioside C, rebaudioside D, rebaudioside E, rebaudioside F, dulcoside A, steviolbioside, rubusoside, as well as other steviol glycosides found in *Stevia rebaudiana* Bertoni plant and mixtures thereof, stevia extract, Luo Han Guo extract, mogrosides, high-fructose corn syrup, corn syrup, invert sugar, fructooligosaccharides, inulin, inulooligosaccharides, coupling sugar, maltooligosaccharides, maltodextins, corn syrup solids, glucose, maltose, sucrose, lactose, aspartame, saccharin, sucralose, sugar alcohols.

It is to be understood that both the foregoing general description and the following detailed description are exemplary and explanatory and are intended to provide further explanation of the invention as claimed.

DETAILED DESCRIPTION OF THE INVENTION

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In the invention, *Stevia rebaudiana* Bertoni plants, particularly the leaves and stems, were used as a starting material. The "empty" leaf biomass obtained after extraction of steviol glycosides, as well as *Stevia rebaudiana* Bertoni plant stems remaining after "stripping-off" the leaves can be used as a starting material. Therefore, the stevia biomass suitable for the process of the present invention includes pre-processed *Stevia rebaudiana* Bertoni plants (e.g., post-extraction of steviol glycosides) and un-processed *Stevia rebaudiana* Bertoni plants.

The testing of obtained microcrystalline cellulose was conducted according to procedures set in microcrystalline cellulose monograph prepared at the 55th FAO/JECFA meeting (2000) and published in Food and Nutrition Paper 52 Addendum 8 (2000).

In one embodiment of the invention, the starting material is milled using rotary blade grinder to produce particles from 1-50 mm, preferably 5-20 mm in length. Any other equipment capable of reducing large particles into smaller ones can be used in this stage as well.

In one embodiment of the invention the obtained grinded biomass is dispersed in the water and boiled at 100° C. for 0.5-3 hours, preferably 1-1.5 hours, followed by separation of the liquid and biomass. The process is repeated several times until colorless or substantially colorless liquid is obtained. A continuous extracting apparatus, as well as any other equipment known to those skilled in art, may be used for this purpose.

In one embodiment of this invention the separated biomass is subsequently introduced into 10-20% NaOH aqueous solution. The solution is treated in pressurized vessel at 110-180° C., preferably 120-170° C., during 0.1-10 hours, preferably 1-5 hrs to produce pulped biomass. Alternatively other pulping techniques such as biological or organic solvent pulping, mechanical, thermomechanical, chemo-thermomechanical, chemical pulping such as Kraft process, sulfite process can be used. After thermal treatment the pulped biomass is separated from the liquid and washed with the water till neutral pH of washing water is achieved.

In one embodiment of this invention the washed biomass is treated with bleaching agent. Various bleaching agents such as hydrogen peroxide, ozone, chlorine, sodium hypochlorite, chlorine oxide, enzymes may be used. However it is preferred to use chlorine-free bleaching agents.

In one embodiment of present invention the bleaching of pulped biomass is achieved by using 10-30%, preferably 20-25%, hydrogen peroxide. The biomass was suspended in 0.5-5, preferably 1-3 volumes of hydrogen peroxide and incubated at 80-150° C., preferably 100-120° C., during 0.1-3 hours, preferably 0.5-1.5 hours. The bleached biomass was subsequently separated from liquid and washed with water.

In one embodiment of this invention, the obtained biomass was subjected to partial depolimerization. Various agents capable of depolimerizing the cellulose, such as mineral acids and enzymes, can be utilized for this stage.

In one embodiment of this invention the depolimerization is achieved by 1-20%, preferably 5-15% hydrochloric acid. The ratio of bleached biomass to acid solution is 1:0.5 to 1:5, preferably 1:1 to 1:3. The temperature of depolimerization process is 50-120° C., preferably 80-100° C. during 0.1-5 hours, preferably 0.5-2 hours.

In one embodiment the obtained depolimerized cellulose is separated from acid solution and washed with water until neutral pH is achieved. The obtained solids are suspended in 1-3 volumes of water and spray dried at inlet temperature of 180° C. and outlet temperature of 100° C.

In one embodiment of present invention a stevia sweetener is added to depolimerized cellulose slurry. The ratio of stevia sweetener to depolimerized cellulose on dry weigh basis is 1:50 to 1:400 (wt), preferably 1:100 to 1:300.

Any other drying techniques such as flash drying, or vacuum drying can be used for the drying of the slurry as well.

Non-limiting examples of stevia sweeteners include stevia extract, steviol glycosides, stevioside, rebaudioside A, rebaudioside B, rebaudioside C, rebaudioside D, rebaudioside E, rebaudioside F, dulcoside A, steviolbioside, rubusoside, as well as other steviol glycosides found in *Stevia rebaudiana* Bertoni plant and mixtures thereof.

Alternatively the cellulose produced by the method of this invention can be processed into other food ingredients by techniques known to those skilled in art. Non limiting examples of such ingredients include, water soluble cellulose, carboxymethyl cellulose, methylcellulose, hydroxypropylcellulose, hydroxypropyl-methylcellulose, ethylmethylcellulose as well as cellobiose, glucose etc.

The products of present invention can be used as bulking agents, sweeteners, flavor enhancers in various food and beverage products. Non-limiting examples of food and beverage products include tabletop sweeteners, carbonated soft drinks, ready to drink beverages, energy drinks, isotonic drinks, low-calorie drinks, zero-calorie drinks, sports drinks, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, fruits and vegetables.

Additionally the products can be used in drug or pharmaceutical preparations and cosmetics, including but not limited to toothpaste, mouthwash, cough syrup, chewable tablets, lozenges, vitamin preparations, and the like.

The products can be used "as-is" or in combination with other sweeteners, flavors and food ingredients.

Non-limiting examples of sweeteners include steviol glycosides, stevioside, rebaudioside A, rebaudioside B, rebaudioside C, rebaudioside D, rebaudioside E, rebaudioside F, dulcoside A, steviolbioside, rubusoside, as well as other steviol glycosides found in *Stevia rebaudiana* Bertoni plant and mixtures thereof, stevia extract, Luo Han Guo extract, mogrosides, high-fructose corn syrup, corn syrup, invert sugar, fructooligosaccharides, inulin, inulooligosaccharides, coupling sugar, maltooligosaccharides, maltodextins, corn syrup solids, glucose, maltose, sucrose, lactose, aspartame, saccharin, sucralose, sugar alcohols.

Non-limiting examples of flavors include lemon, orange, fruit, banana, grape, pear, pineapple, bitter almond, cola, cinnamon, sugar, cotton candy, vanilla flavors.

Non-limiting examples of other food ingredients include flavors, acidulants, organic and amino acids, coloring agents, bulking agents, modified starches, gums, texturizers, preservatives, antioxidants, emulsifiers, stabilisers, thickeners, gelling agents.

The following examples illustrate various embodiments of the invention. It will be understood that the invention is not limited to the materials, proportions, conditions and procedures set forth in the examples, which are only illustrative.

EXAMPLE 1

Preparation of Stevia Ingredient 1 kg of *Stevia rebaudiana* plant dried leaves were grinded into pieces of approx 10 mm, suspended in 5 L of water and boiled for 1 hour. The liquid was removed and the separated biomass was resuspended in the water and treated as described above. The process was repeated 5 times. The resulted biomass was suspended in 3 L 15% NaOH solution and placed into autoclave for pulping at 150° C. for 2 hrs. The obtained pulped biomass is separated from liquid and washed with deionized water till neutral pH of washing water. The washed pulp was suspended in 3 L of 20% hydrogen peroxide and treated for 1 hr at 100° C. The bleached pulp was washed with water and suspended in 3 L 10% hydrochloric acid. The mixture was heated to 90° C. for 1 hr. The obtained mixture was strained through 60 mesh sieve and then filtered through grade 1 filter paper. The solids recovered on the filter paper were washed with deionozed water till neutral pH of washing water was achieved. The washed were suspended in 1.5 L of water and spray dried by YC-015 laboratory spray drier (Shanghai Pilotech Instrument & Equipment Co. Ltd., China) operating at 180° C. inlet and 100° C. outlet temperature. About 480 g of free flowing microcrystalline cellulose was obtained.

EXAMPLE 2

Preparation of Stevia Ingredient 1 kg of *Stevia rebaudiana* plant dried stems were processed similarly to leaves according to EXAMPLE 1. About 670 g of free flowing microcrystalline cellulose was obtained.

EXAMPLE 3

Preparation of Stevia Composition

About 500 g of microcrystalline cellulose prepared according to example 1 or 2 was added to 1500 mL water solution containing 2.5 g of rebaudioside A produced by PureCircle Sdn. Bhd. (Malaysia) with purity of 99.5% (dry basis). The mixture was spray dried to yield about 490 g of dry powder.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

I claim:

1. A product comprising:
   stevia-derived microcrystalline cellulose; and
   a flavoring agent.
2. The product of claim 1, wherein the stevia-derived microcrystalline cellulose is obtained from a stevia biomass by a process, said process comprising the steps of:
   (a) removing water-insoluble components from a stevia biomass;
   (b) incubating the water-insoluble, components in an alkaline solution to produce a pulp;
   (c) washing the pulp to obtain a washed pulp;
   (d) bleaching the washed pulp to obtain a bleached pulp; and
   (e) separating cellulose from the bleached pulp.
3. The product of claim 2, wherein the process further comprises the steps of:
   (f) depolymerizing the cellulose to obtain a depolymerized cellulose;
   (g) washing the depolymerized cellulose to yield cellulose crystals; and
   (h) suspending the cellulose crystals in water and spray-drying to yield the stevia-derived microcrystalline cellulose ingredient.
4. The product of claim 1, said product further comprising a sweetener.
5. The product of claim 4, wherein the sweetener is selected from the group consisting of stevia extract, steviol glycosides, stevioside, rebaudioside A, rebaudioside B, rebaudioside C, rebaudioside D, rebaudioside E, rebaudioside F, dulcoside A, steviolbioside, rubusoside, other steviol glycosides found in *Stevia rebaudiana* Bertoni plant and mixtures thereof, Luo Han Guo extract, mogrosides, high-fructose corn syrup, corn syrup, invert sugar, fructooligosaccharides, inulin, inulooligosaccharides, coupling sugar, maltooligosaccharides, maltodextins, corn syrup solids, glucose, maltose, sucrose, lactose, aspartame, saccharin, sucralose, sugar alcohols, and a combination thereof.
6. The product of claim 1, wherein the flavoring agent is selected from the group consisting of lemon, orange, fruit, banana, grape, pear, pineapple, mango, bitter almond, cola, cinnamon, sugar, cotton candy, vanilla, and a combination thereof.
7. The product of claim 1, wherein the product is food, beverage, cosmetics or pharmaceutics.
8. A product comprising:
   stevia-derived microcrystalline cellulose; and
   a food ingredient.
9. The product of claim 8, wherein the stevia-derived microcrystalline cellulose is obtained from a stevia biomass by a process, said process comprising the steps of:
   (a) removing water-insoluble components from a stevia biomass;
   (b) incubating the water-insoluble components in an alkaline solution to produce a pulp;
   (e) washing the pulp to obtain a washed pulp;
   (d) bleaching the washed pulp to obtain a bleached pulp; and
   (e) separating cellulose from the bleached pulp.
10. The product of claim 9, wherein the process further comprises the steps of:
    (f) depolymerizing the cellulose to obtain a depolymerized cellulose;
    (g) washing the depolymerized cellulose to yield cellulose crystals; and
    (h) suspending the cellulose crystals in water and spray-drying to yield the stevia-derived microcrystalline cellulose ingredient.
11. The product of claim 8, said product further comprising a sweetener.
12. The product of claim 11, wherein the sweetener is selected from the group consisting of stevia extract, steviol glycosides, stevioside, rebaudioside A, rebaudioside B, rebaudioside C, rebaudioside D, rebaudioside E, rebaudioside F, dulcoside A, steviolbioside, rubusoside, other steviol glycosides found in *Stevia rebaudiana* Bertoni plant and mixtures thereof, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols, and a combination thereof.

13. The product of claim 8, wherein the food ingredient is selected from the group consisting of acidulants, organic and amino acids, coloring agents, bulking agents, modified starches, gums, texturizers, preservatives, antioxidants, emulsifiers, stabilisers, thickeners, gelling agents, and a combination thereof.

* * * * *